United States Patent [19]

Lickle

[11] Patent Number: 5,016,293
[45] Date of Patent: May 21, 1991

[54] AIR INDUCTION SYSTEM FOR GOGGLE

[76] Inventor: Brett Lickle, 115 Lua Hine Pl., Haiku, Hi. 96708

[21] Appl. No.: 557,028

[22] Filed: Jul. 25, 1990

[51] Int. Cl.⁵ .................................................. A61F 9/02
[52] U.S. Cl. .......................................... 2/436; 2/435; 2/448
[58] Field of Search .................. 2/435, 436, 437, 438, 2/448, 452

[56] References Cited

U.S. PATENT DOCUMENTS

| | | | |
|---|---|---|---|
| 2,027,037 | 1/1936 | Gottlieb | 2/13 |
| 2,410,184 | 10/1946 | Schauweker | 2/437 |
| 3,036,310 | 5/1962 | Young | 2/436 |
| 3,160,735 | 12/1964 | Aufricht | 2/435 |
| 3,497,294 | 2/1970 | Volk | 351/41 |
| 3,943,925 | 3/1976 | Leight | 2/423 |
| 4,174,155 | 11/1979 | Herman | 351/158 |
| 4,317,240 | 3/1982 | Angerman et al. | 2/436 |
| 4,435,852 | 3/1984 | Nesler | 2/436 |
| 4,751,746 | 6/1988 | Rustin | 2/13 |

Primary Examiner—Werner H. Schroeder
Assistant Examiner—Michael A. Neas
Attorney, Agent, or Firm—Watson, Cole, Grindle & Watson

[57] ABSTRACT

A spacer is slidably mounted to the headband of a goggle. The spacer comprises a block formed of a body which in use is captured between the headband and the head of the user. The block has an elongated contoured inboard head engaging surface and an outboard frame engaging portion spaced therefrom. In a forward position, adjacent the goggle, the block supports the goggle in spaced relation with the face or head of the wearer to thereby allow ventilation thereof. When the block is in a retracted position the goggle rests against the face or head of the user.

9 Claims, 2 Drawing Sheets

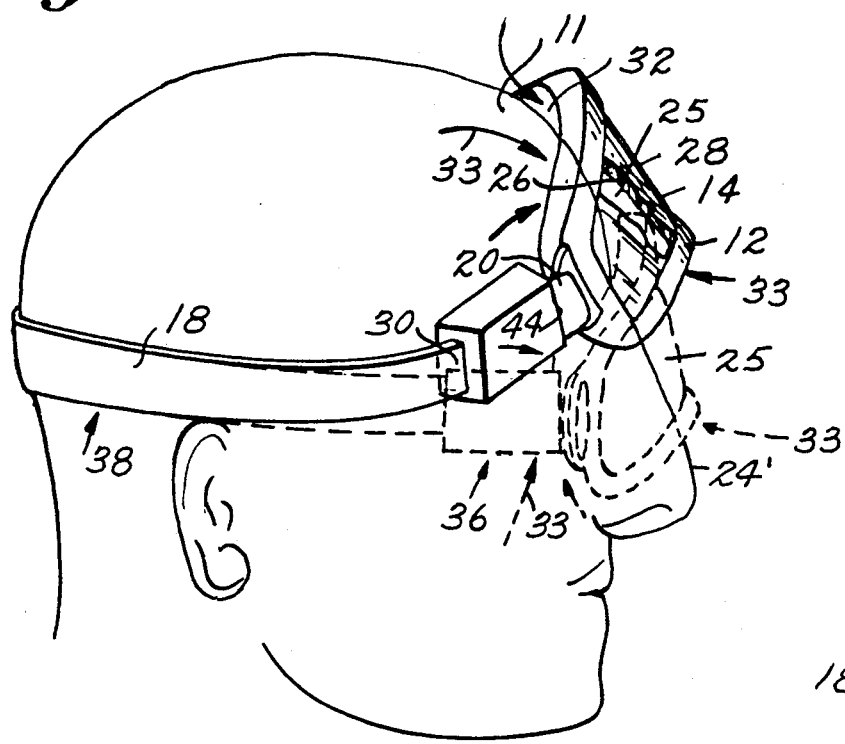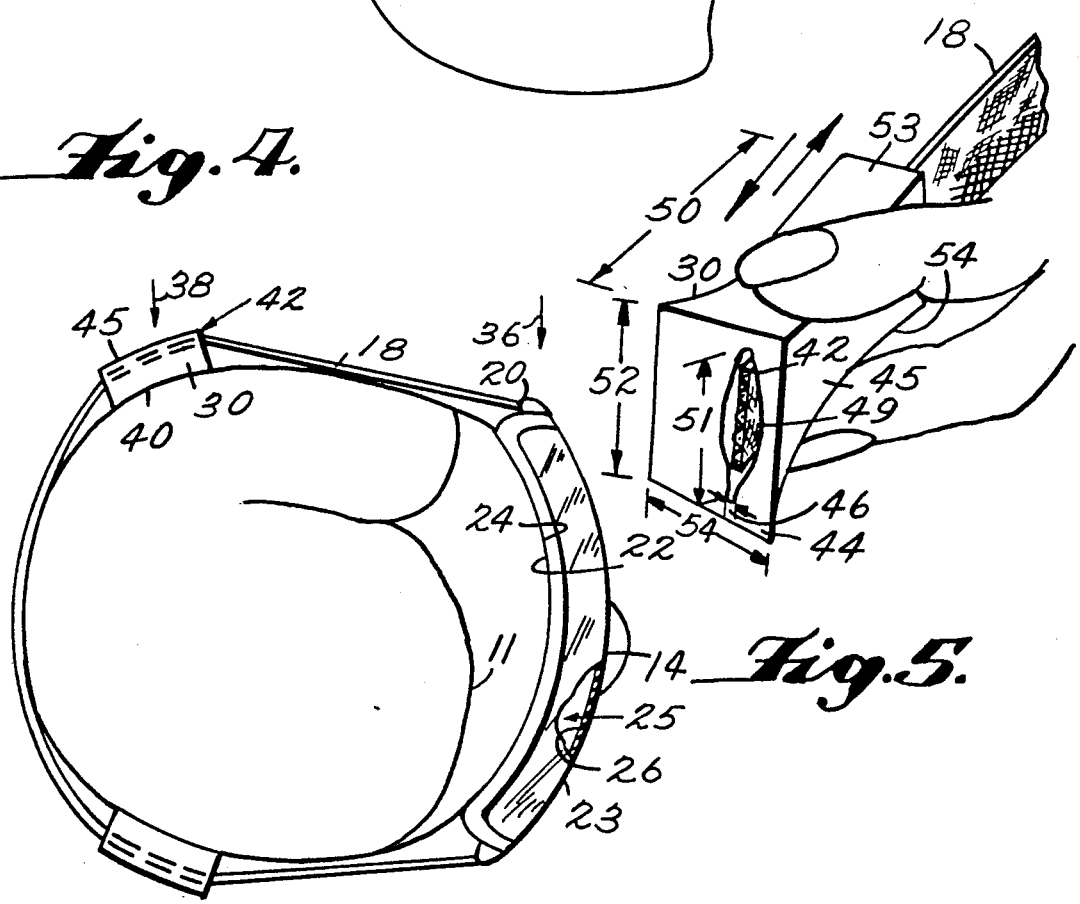

AIR INDUCTION SYSTEM FOR GOGGLE

BACKGROUND OF THE INVENTION

The invention relates to improvements in a ski goggle and the like and in particular to a device for allowing the goggle to be cleared or defogged of condensed moisture formed on the internal viewing surface thereof while in use or in resting period while on the head.

A conventional ski goggle is secured onto the head of a user by a headband which is attached to lateral sides of the goggle by various conventional methods. The headband secures the goggle onto the head in various positions or about the neck. In particular, the headband allows the goggle to be positioned over the eyes when in use or on the forehead or ski hat when not in use. Typical goggle designs employ a contoured face engaging surface which seals the goggle against the face, hat if worn, or head and hair in or near the viewing position and thereby forms a generally closed unventilated volume. Oftentimes during skiing, vaporous moisture from perspiration and snow is trapped in the closed volume. The vaporous moisture tends to condense on the warm inside surface of the goggle lens which causes the goggle to fog up and thereby impair the vision of the user.

Normally it is necessary to stop skiing, remove and pump the goggle to create air flow through the inside or retrieve a wipe in order clean the goggle. Another less effective way of cleaning the goggle includes wiping the inside of the lens with a gloved or ungloved finger, but the results are typically unsatisfactory. In any event, the necessity to frequently defog the lens becomes burdensome and reduces the enjoyment of the sport. In addition, there is strong incentive not to defog the lens, but to simply ignore the problem until reduced visibility becomes intolerable. This presents a danger to the user as well as others nearby.

In Gottlieb, U.S. Pat. No. 2,027,037 the problem of condensation on spectacle lenses is addressed. In the arrangement, guards are attached to the spectacle rims in such a way that the lenses are spaced out of contact with the face. The patent does not address the problems associated with a tightly fitting goggle and a flexible headband.

In Augerman et al., U.S. Pat. No. 4,317,240 a sports goggle is provided with an anterior frame section which carries the lens and a posterior frame section which carries the nose bridge and temples. The distal ends of the temples are connected by means of a flexible headband. Spacing from the face is maintained by the rigid hinge portions on the posterior frame and a stud on the nose piece. The problem of a confined or unventilated goggle is not addressed.

Schauweker, U.S. Pat. No. 2,410,184 discloses an eye protection device, for example, welders goggles which have permanent vent openings in the side of each goggle element.

Volk, U.S. Pat. No. 3,497,294 discloses conventional eyeglasses employing temple mounted vanes which may be extended outwardly to direct air across the interior surface of the glasses.

Leight, U.S. Pat. No. 3,943,925 and Herman, U.S. Pat. No. 4,174,155 describe spectacles which carry slidable ear protectors on the temples. Rustin, U.S. Pat. No. 4,751,746 also describes ear protectors which are mounted on the temples and held in position by means of a clip which attaches to the lens frame.

The prior methods do not provide for a convenient, effective, stylish and comfortable method for clearing and prevention of fogging in a ski goggle.

SUMMARY OF THE INVENTION

In one embodiment, the invention comprises an air induction system for ventilating a goggle. A spacer is slidably mounted to the headband securing the goggle on the wearer. The spacer comprises a block which in use is captured between the headband and the head of the user. The block has an elongated contoured inboard head engaging surface and an outboard frame engaging portion spaced therefrom. In a forward position, adjacent the goggle, the block supports the goggle in spaced relation with the face or hat or head of the wearer to thereby allow ventilation thereof for fog prevention. When the block is in a retracted position the goggle rests against the face of the user. In a preferred embodiment the block is formed of a resilient material having an elongated slot near its exterior or outboard side for receiving the headband therethrough. The slot is closely spaced with respect to the outboard frame engaging portions by an amount selected to allow the block to space the goggle from the head without unduly stressing the headband.

DESCRIPTION OF THE DRAWINGS

FIG. 2 is a fragmented side view of the air induction system of the present invention in which the goggle is shown resting against the hair and head in solid line and against the face in phantom lines;

FIG. 4 is a schematic plan view of the arrangement illustrated in FIG. 3 with the spacers retracted and the goggle resting against the face of the user; and FIG. 5 shows the spacer deformed by finger pressure to thereby open the slot to receive the headband.

DESCRIPTION OF THE INVENTION

Figure 1:
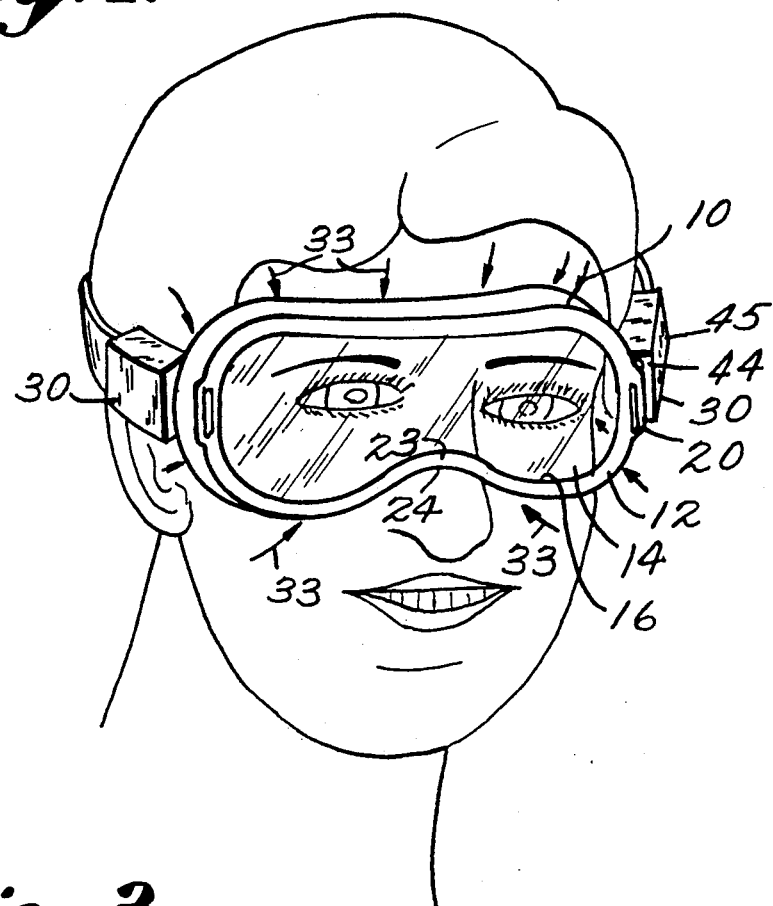
FIG. 1 is a perspective view of the air induction system for goggle of the present invention in which slidable spacers are located on the headband of a ski goggle.

FIG. 1 illustrates in perspective an embodiment of the invention in which a goggle 10 comprising a frame portion 12 supports a lens 14 in an opening 16 forming a viewing area for the user. A headband 18 which may be a one-piece elastic element, as shown, or a two-piece fabric element is attached at its opposite ends to lateral sides or temples 20 of the frame 12. An inboard or contoured surface 22 including bridge piece 23 of the goggle 10 is adapted to rest against a corresponding contoured portion of the face 24 and nose 24' of the user. The contoured surface 22 forms a seal with the face 24, or head and hair 11 of the user forming a more or less closed chamber 25.

Alternatively, while not in the viewing position, as shown in solid lines in FIG. 2, goggle 10 may rest atop the head and hair 11. It is equally if not more important to prevent fogging when the goggle is against the head or hair 11 because heat from the head combined with moisture and perspiration tends to seriously fog the goggle 10.

The lens 14 has respective internal and external surfaces 26 and 28. The user's perspiration and other forms of moisture in the environment tend to condense as a film on the internal surface 26 of the lens. This occurs because the moisture laden air within the chamber 25 tends to be at a higher temperature than the ambient and thus is capable of containing more moisture than the surrounding atmosphere. Accordingly, when the moisture laden air makes contact with the internal surface 26 of the lens 14 excess moisture condenses on it causing it to fog.

Figure 3:
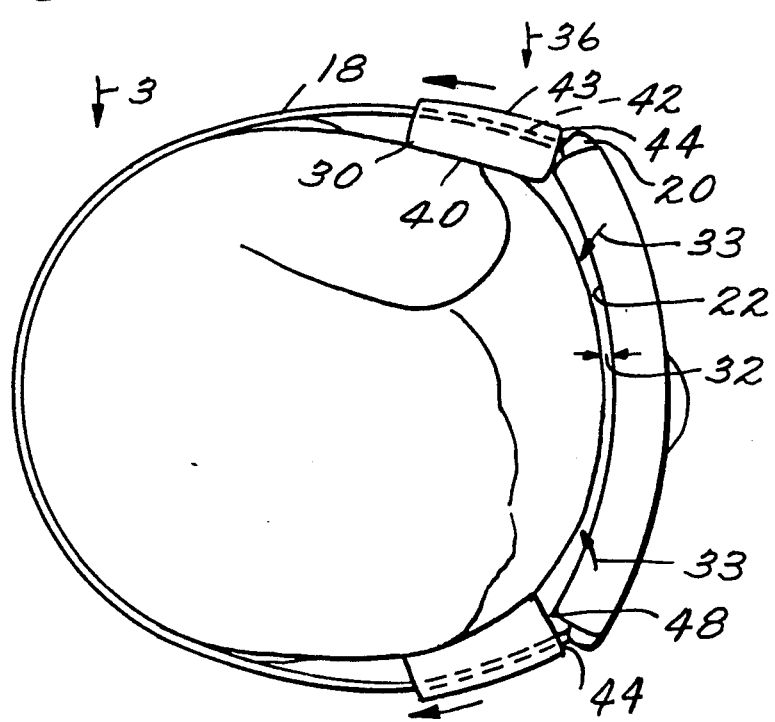
FIG. 3 is a top plan view of the air induction of the present invention with the spacers in the forward position for providing ventilation for the goggle.

In order to prevent or reduce such condensation, spacers 30 are slidably positioned on the headband 18. The spacers 30 may be located in a forward position 36 as shown in FIG. 3 adjacent the temple portions 20 of the frame, or the spacers 30 may be located in a retracted position 38 away from the temples 20 as shown in FIG. 4. In the forward position 36 the spacers 30 engage and support the frame 12 of the goggle 10 away from the face 24 or head and hair 11 of the user. In the viewing position the goggle remains supported on by the bridge piece 23 resting on the nose 24'. The spacers 30 provide a gap 32 in the region between the frame 12 and the face 24 or head and hair 11 as shown. The gap 32 allows the moisture laden air trapped in the chamber 25 to escape from the chamber 25 about the top, sides and bottom of the goggle and to be replaced by ambient air shown by arrows 33 (FIG. 3) whether the goggle 10 be on the head and hair 11 or on the face 24. When in the retracted position 38, the spacers 30 are disengaged from the frame 12 of the goggle 10 thereby allowing the goggle to rest against the face 24 or head and hair 11 of the user (FIG. 4).

Each spacer 30 may be formed of a resilient rubber or soft plastic material in the form of a generally rectangular block having a contoured head or face engaging side 40. The spacer 30 has an elongated through slot 42 for receiving the headband 18 so that the head engaging surface 40 faces inwardly of the goggle 10 in confronting relationship with the head and hair 11 or face 24 as shown. A forward surface 44 of the spacer 30 engages a terminal portion 48 of the inboard contoured surface 22 of the frame 12 when the spacer 30 is moved to the forward position 36 (FIG. 3). In the forward position 36 the face engaging surface 40 of the spacer 30 confronts the head or face 24 of the user. The flexible headband 18 allows the spacer 30 to lie smoothly and comfortably against the head while remaining captured by the headband 18. The slot 42 is spaced from the head engaging surface 40 and relatively close to the outboard surface 45. The arrangement allows the spacer 30 to support the goggle 10 away from the face 24 and head 11 without unduly stressing the headband 18. This also allows for a more comfortable fit against the head. The outboard surface 45 of the spacer 30 may also carry a decorative designer logo which may be useful for advertising purposes and the like.

In the retracted position 38 the spacer 30 likewise lies against the head 24 as shown. The goggle 10 at the same time rests against the head and hair 11 or the face 24 as shown in FIG. 4.

The spacer 30 may be conveniently sized so that it is easily grasped by the gloved hand of the skier and so that it may be moved between the respective forwarded and retracted positions 36 and 38 without difficulty (FIG. 5). For example, the spacer 30 may have a length dimension 50 and a width dimension 52 each of which are about 1 inch. The spacer has a thickness dimension 54 that varies in accordance with the contour of the curved face engaging surface 40. At the ends, the thickness dimension 54 may be about 0.5 inch which depending on the goggle configuration is sufficient to support the goggle away from the face 24 so that the resulting gap 32 is approximately 0.25 inch. The thickness of the spacer 30 at the midpoint of the surface 40 is such that the overall curvature thereof is approximately that of the average human. The width 46 of the slot 42 may be sized to suitably receive the headband 18 therein with a frictional force sufficient to keep the block in place. For example, the slot 42 is about as wide as a typical headband. Internal surfaces 49 of the slot 42 thereof frictionally engage the sides of the headband 18. The height 50 of the slot 42 may be conveniently sized to receive any number of headbands.

The spacers 30, as noted above, are formed of a resilient plastic or rubber material. In the embodiment shown in FIG. 5, the flexibility allows the slot 42 to be deformed and thereby enlarged by lateral pressure against the upper and lower sides 52-54 of the block. The enlargement of the slot 42 allows the headband 18 to be easily threaded therethrough. Alternatively, a longitudinal slot may be provided in the outer wall of the spacer in communication with the slot that it may be readily installed on any continuous headband. Alternatively, the spacer may be formed with an integral hinged cover adapted to close over the open slot.

While there has been described whether present invention are considered the preferred embodiment of the present invention it will be apparent to those given in the art that various changes and modifications may be made therein without departing from the invention and is intended in the appended claims to cover such modifications as fall within the true spirit and scope of the invention.

What is claimed is:

1. A goggle comprising:
   a lens;
   a frame for securing the lens therein;
   a headband secured to lateral portions of the frame for securing the frame in position in contact against the head of a wearer; and
   slider means slidably positioned on the headband proximate the frame for supporting the frame in a spaced relationship with respect to the head of the wearer to thereby allow ventilation of the goggle when so positioned, said slider means being retractable along said headband away from the frame for allowing the goggle to rest against the head of the wearer when so positioned.

2. The goggle of claim 1 wherein the slider means comprises a pair of slider blocks, one for each side of the goggle.

3. A spacer for a goggle secured to the head of a wearer by means of a headband, said spacer comprising a block having a selected thickness and an elongated inboard head engaging surface and an outboard headband engaging portion spaced from the inboard surface;
   means for securing the block slidably onto the headband between respective engaged and retracted positions, said spacer for supporting the goggle in a spaced relationship with respect to the head of the wearer for ventilating the goggle when in the engaged position and allowing the goggle to rest against the head of the wearer when in the retracted position.

4. The spacer of claim 3 wherein the means for securing the block onto the headband comprises an elongated through slot for receiving the headband therethrough.

5. The spacer of claim 4 wherein said head engaging surface is spaced from the slot and is relatively close to the outboard headband engaging portion for allowing the block to support the goggle away from the head without stressing the headband.

6. The spacer of claim 4 wherein the spacer is formed of a resilient deformable material so that the slot is enlarged by pressure applied to the block laterally of said slot to thereby allow for the headband to be easily threaded therethrough.

7. The spacer of claim 6 wherein wall portions of the slot frictionally engage the headband when the block is undeformed.

8. The spacer of claim 4 wherein the head engaging surface is concave for conforming to the shape of the head.

9. The spacer of claim 3 wherein the block includes a forward surface extending from the head engaging surface towards the outboard portion for engaging the goggle when the block is in the engaged position.

* * * * *